US012627938B2

(12) United States Patent
Anderson

(10) Patent No.: US 12,627,938 B2
(45) Date of Patent: May 12, 2026

(54) CALIBRATION OF WEARABLE SOUND-EMITTING DEVICES

(71) Applicant: OIDO, INC., Vancouver, WA (US)

(72) Inventor: Jason Anderson, Vancouver, WA (US)

(73) Assignee: OIDO, INC., Vancouver, WA (US)

( * ) Notice: Subject to any disclaimer, the term of this patent is extended or adjusted under 35 U.S.C. 154(b) by 131 days.

(21) Appl. No.: 18/529,288

(22) Filed: Dec. 5, 2023

(65) Prior Publication Data

US 2024/0397275 A1     Nov. 28, 2024

Related U.S. Application Data

(60) Provisional application No. 63/386,158, filed on Dec. 5, 2022.

(51) Int. Cl.
H04R 25/00     (2006.01)
A61B 5/12      (2006.01)
G06F 3/16      (2006.01)

(52) U.S. Cl.
CPC ............. H04R 25/70 (2013.01); A61B 5/123 (2013.01); G06F 3/165 (2013.01); H04R 25/558 (2013.01); H04R 2225/55 (2013.01)

(58) Field of Classification Search
None
See application file for complete search history.

(56) References Cited

U.S. PATENT DOCUMENTS

| | | | | |
|---|---|---|---|---|
| 8,948,426 | B2 * | 2/2015 | Thomasson ............ | A61B 5/121 381/328 |
| 9,918,171 | B2 * | 3/2018 | Shennib ................. | H04R 25/70 |
| 10,341,790 | B2 * | 7/2019 | Shennib ............... | H04R 25/554 |
| 10,734,964 | B2 * | 8/2020 | Shin ........................ | H04R 25/75 |
| 11,357,424 | B2 * | 6/2022 | Chang .................. | A61B 5/7203 |
| 11,665,488 | B2 * | 5/2023 | Greenberg ........... | A61B 5/7264 381/314 |
| 11,979,512 | B2 * | 5/2024 | Jarng ..................... | H04R 25/70 |
| 11,991,570 | B2 * | 5/2024 | Hao .................. | H04W 36/0072 |
| 2006/0045281 | A1 * | 3/2006 | Korneluk ................. | H04R 5/04 381/60 |
| 2006/0215844 | A1 * | 9/2006 | Voss ........................ | H04R 25/70 381/60 |

(Continued)

FOREIGN PATENT DOCUMENTS

| | | | | |
|---|---|---|---|---|
| CN | | 115175076 A | * 10/2022 | ............. H04R 25/30 |

OTHER PUBLICATIONS

English Language Translation of CN115175076A, pp. 1-25 (Year: 2022).*

*Primary Examiner* — Paul W Huber
(74) *Attorney, Agent, or Firm* — Stoel Rives LLP

(57)     ABSTRACT

The present disclosure relates to a hearing aid hearing test and calibration system. An exemplary system includes: a hearing aid that amplifies sound and further plays the amplified sound; and a computing device that communicates with the hearing aid, and performs a fitting process responsive to a user's activation. The fitting process includes: setting a test frequency and a test amplitude; causing the hearing aid to play a sound at the test frequency and the test amplitude; prompting the user to respond as to whether the user is able to hear; and upon a positive or negative response from the user, causing the hearing aid to change the amplitude to calibrate.

17 Claims, 14 Drawing Sheets

(56)                    References Cited

U.S. PATENT DOCUMENTS

| | | | |
|---|---|---|---|
| 2010/0119093 A1* | 5/2010 | Uzuanis | H04R 25/70 |
| | | | 455/41.2 |
| 2013/0182855 A1* | 7/2013 | Choi | A61B 5/121 |
| | | | 381/23.1 |
| 2022/0369053 A1* | 11/2022 | Austin | H04R 25/505 |
| 2022/0370249 A1* | 11/2022 | Pangarkar | G10K 11/17873 |
| 2024/0064487 A1* | 2/2024 | Uppuluri | H04S 7/307 |
| 2024/0276160 A1* | 8/2024 | Wu | H04R 25/558 |
| 2024/0369054 A1* | 11/2024 | Cangioli | F04D 25/06 |

* cited by examiner

1202

1204

1206

1208

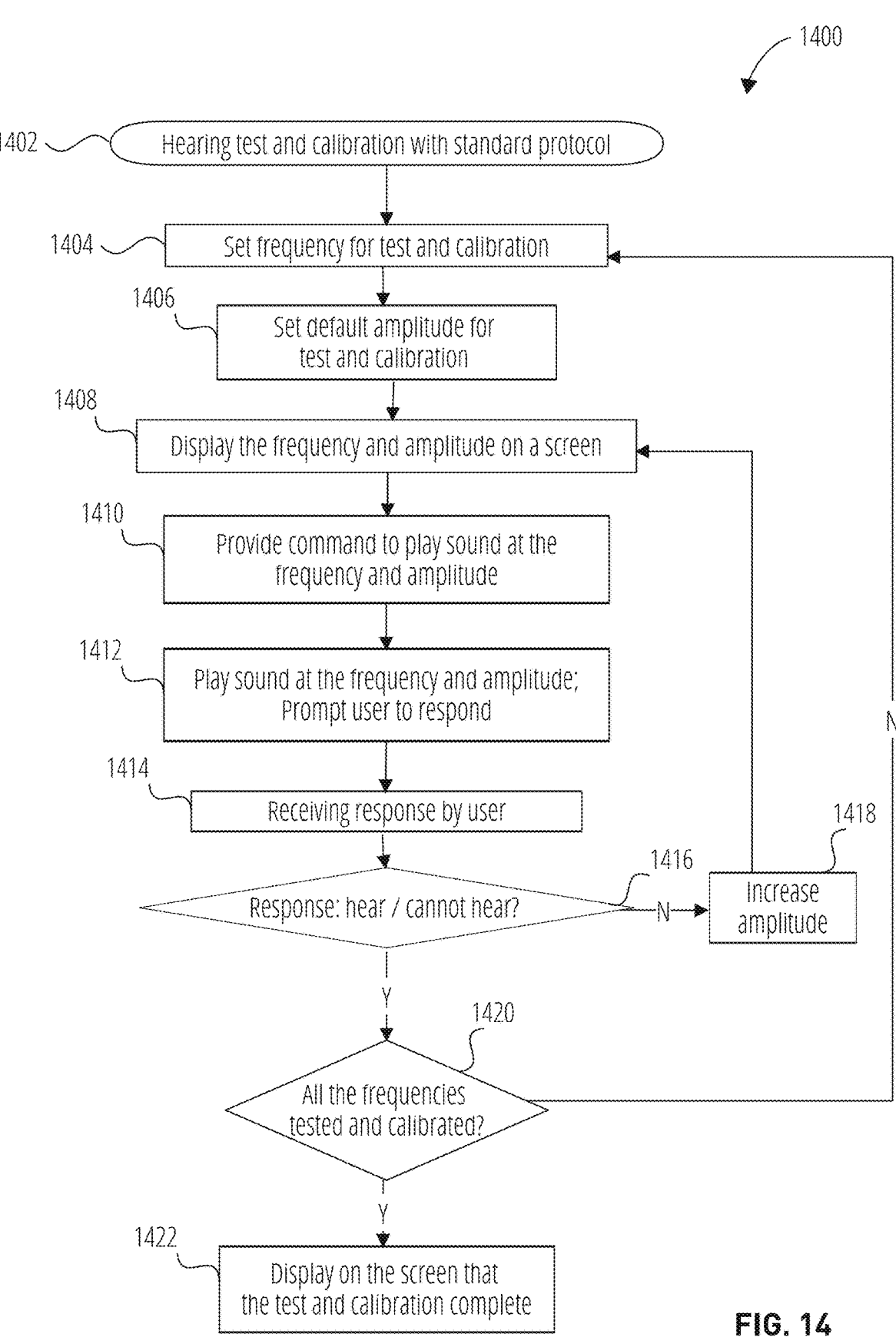

1400

1402 — Hearing test and calibration with standard protocol

1404 — Set frequency for test and calibration

1406 — Set default amplitude for test and calibration

1408 — Display the frequency and amplitude on a screen

1410 — Provide command to play sound at the frequency and amplitude

1412 — Play sound at the frequency and amplitude; Prompt user to respond

1414 — Receiving response by user

1416 — Response: hear / cannot hear?    N

1418 — Increase amplitude    N

1420 — All the frequencies tested and calibrated?    Y

1422 — Display on the screen that the test and calibration complete

CALIBRATION OF WEARABLE SOUND-EMITTING DEVICES

CROSS-REFERENCE TO RELATED APPLICATION(S)

This application claims priority to U.S. Provisional Application No. 63/386,158 filed Dec. 5, 2022, which is incorporated herein by reference, in its entirety, for any purpose.

TECHNICAL FIELD

This disclosure relates generally to user calibration of hearing aids, in-ear or over-ear headphones, and other wearable sound modification and/or amplification devices.

BACKGROUND INFORMATION

Existing hearing aid fitting has two primary steps. According to audiology best practices, the first major step in fitting a hearing aid is to conduct a pure tone audiometry test. Audiometric threshold data, also known as pure-tone testing, has been used since the 1920s to categorize the degree and type of hearing loss. Audiometric testing utilizes various intensities of sound emitted over a range of frequencies to determine deficits in hearing, which is plotted on a graph, also known as an audiogram. The characteristic configurations and patterns produced on the audiogram can guide healthcare practitioners in understanding the mechanism of an individual's hearing loss.

After reading the audiogram, an audiologist will then program a hearing aid based on patient hearing thresholds and move on to the second major step in fitting best practices: real ear measures. Real ear measurement is a process that audiologists use to determine the efficacy of a hearing aid once in a patient's ear. This step is essential due to everyone's unique ear canal geometry. Audiologists perform real ear measures by placing a microphone probe in an individual's ear canal to measure the output of the hearing aid at the ear drum. Once the real ear measures have been recorded, the audiologist then adjusts the hearing aid to the patient's specific needs.

SUMMARY OF THE DISCLOSURE

Disclosed are techniques to remove the need to employ expensive real ear measurement equipment by enabling individuals to replicate the results of audiology best practices without the need for expensive equipment or training.

Embodiments described herein address the problem of the time and expense involved in the current methods for providing hearing aids and other such devices to customers and the calibration of same for each individual customer.

Additional aspects and advantages will be apparent from the following detailed description of embodiments, which proceeds with reference to the accompanying drawings.

BRIEF DESCRIPTION OF THE DRAWING FIGURES

To easily identify the discussion of any particular element or act, the most significant digit or digits in a reference number refer to the figure number in which that element is first introduced.

FIG. 14 shows an example process 1400 for performing a hearing test and calibration using standard protocol, according to one embodiment.

DETAILED DESCRIPTION OF EMBODIMENTS

In the following description, various embodiments will be described. For purposes of explanation, specific configurations and details are set forth in order to provide a thorough understanding of the embodiments. However, it will also be apparent to skilled persons that the embodiments may be practiced without the specific details. Furthermore, well-known features may be omitted or simplified in order not to obscure the embodiment being described.

While the following preferred embodiments refer specifically to hearing aids as an example, it should be appreciated that the same methods may apply to other wearable sound modification and/or amplification devices and no limitation is intended.

Figure 1:
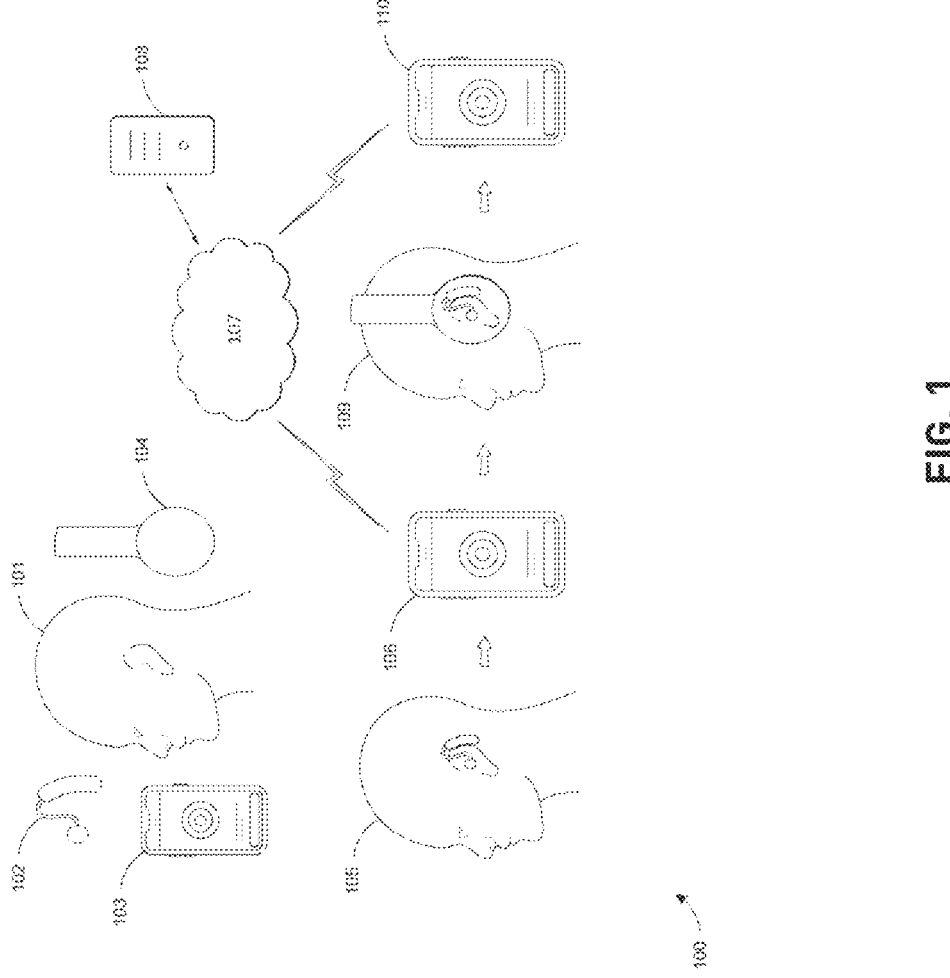
FIG. 1 is a block diagram of an example system in accordance with one embodiment.

FIG. 1 is a block diagram of an example system 100 in accordance with one embodiment. FIG. 1 shows a user 101 of the system 100 and the system 100 including a hearing aid 102, a mobile device 103, and over-ear headphones 104 in communication with the mobile device 103. The hearing aid 102 in a normal operation may receive sound in the air, amplify the sound, and play the amplified sound in the ear(s) of the user 101. In this embodiment, the mobile device 103, such as a smartphone, may run a hearing aid application (hereinafter referred to as "app") that performs hearing tests and calibration processes using the hearing aid 102. In some embodiments, the hearing tests and calibration processes may be performed by any computing device, such as a tablet, a wearable fitness device, a computer such as a laptop or desktop, etc., using the hearing aid 102. In some embodiments, the mobile device 103 may communicate via a communications link 107, such as an internet or some other network, that connects the mobile device 103 to a remote server 108 in performing the hearing tests and calibration processes. In some embodiments, the mobile device 103 may internally perform functions of the hearing tests and calibration processes.

In a standard fitting preparation 105, the user 101 of the system 100 connects the hearing aid 102 with the mobile device 103 wirelessly (e.g., Bluetooth, near field communication (NFC), Wi-Fi, etc.) or with one or more wires, and wears the hearing aid 102. There is no particular order of wearing the hearing aid 102 and connecting the hearing aid 102 with the mobile device 103.

In a standard fitting 106 including an initial hearing test and calibration process, the user 101 starts the initial hearing test on the mobile device 103, and the mobile device 103 may perform the initial hearing test by causing the hearing aid 102 to play a sound at a frequency based on a standard protocol. In some embodiments, the standard protocol may be equivalent to pure-tone threshold audiometry taught in guidelines (American Speech-Language-Hearing Association, URL "https://www.asha.org/policy/gl2005-00014," hereinafter referred to as "ASLH guidelines") for multiple frequencies. In some examples, air-conduction type hearing aids may provide sound signals at frequencies, such as 250, 500, 1,000, 2,000, 3,000, 4,000, 6,000, and 8,000 Hz (125 Hz under some circumstances). In some examples, bone-conduction type hearing aids may provide sound signals at frequencies with octave intervals from 250 Hz to 4,000 Hz and at 3,000 Hz as needed. In some embodiments, the hearing aid 102 may store sound signals at the above predetermined frequencies used for the initial hearing test, and the mobile device 103 may transmit a command instructing the hearing aid 102 to play a sound at one of these frequencies in the protocol, and the hearing aid 102 may play the sound. In some embodiments, the mobile device 103 may provide a sound signal at each of these frequencies in the protocol, and the hearing aid 102 may play the sound.

The hearing aid 102 plays the sound for each frequency at a reference amplitude for a predetermined time (1-2 seconds, for example). The mobile device 102 may allow the user 101 to indicate whether the user 101 can hear the sound. In some embodiments, the mobile device 102 may display an elapsed time of playing the sound and an entry, such as a touch button or an icon of "can hear" on its screen. If the user 101 enters a response indicating that the user 101 can hear the sound, the mobile device 103 may cause the hearing aid 102 to play the sound with a reduced amplitude at a predetermined interval (e.g., −5 dB steps). If the user 101 fails to enter a response indicating that the user 101 can hear the sound within a predetermined time after the end of the sound or if the user 101 enters a response indicating that the user 101 cannot hear the sound, the mobile device 103 may cause the hearing aid 102 to play the sound with an increased amplitude at a predetermined interval (e.g., 5 dB steps). By repeating the increase and decrease of the amplitude of the sound, the mobile device 103 may obtain a threshold audible amplitude that is a lowest decibel hearing level that the user 101 can hear for each frequency.

Based on the threshold amplitude for each frequency, the hearing aid 102 may perform calibration for each frequency to provide relatively equalized amplitudes across frequencies by compensation of sound pressure for each frequency. The threshold amplitudes for frequencies as a profile of the user 101 may also be stored in the mobile device 103. In some embodiments, the profile of the user 101 may also be transmitted to the remote server 108 via the communications link 107 and the remote server 108 may record the profile of the user 101.

In a real-ear fitting preparation 109, the user 101 may be exposed to a sound source outside the hearing aid 102. In some examples, the user 101 may wear the over-ear headphones 104 as a sound source over the hearing aid 102. In some examples, the user 101 may be in a room with a sound source (e.g., a speaker). In some embodiments, the mobile device 103 or the remote server 108 may have a sound profile, such as frequency response characteristics of the over-ear headphones 104, or the sound source and/or the room.

In a real-ear fitting 110 including a hearing test and calibration process, the user 101 starts the real-ear hearing test on the mobile device 103, and the mobile device 103 may perform the real-ear hearing test by causing the over-ear headphones 104 to play a sound at a frequency based on the standard protocol used in the initial hearing test. In some embodiments, the over-ear headphones 104 may store sound signals at the above predetermined frequencies used for the initial hearing test, and the mobile device 103 may transmit a command instructing the over-ear headphones 104 to play a sound at one of these frequencies in the protocol, and the over-ear headphones 104 may play the sound. In some embodiments, the mobile device 103 may provide a sound signal at each of these frequencies in the protocol, and the over-ear headphones 104 may play the sound.

The over-ear headphones 104 plays the sound for each frequency at a reference amplitude for a predetermined time (e.g., 1-2 seconds). The mobile device 102 may allow the user 101 to indicate whether the user 101 can hear the sound. In some embodiments, the mobile device 102 may display an elapsed time of playing the sound and an entry, such as a touch button or an icon of "can hear" on its screen. If the user 101 enters a response indicating that the user 101 can hear the sound, the mobile device 103 may cause the over-ear headphones 104 to play the sound with a reduced amplitude at a predetermined interval (e.g., −5 dB steps). If the user 101 fails to enter a response indicating that the user 101 can hear the sound within a predetermined time after the end of the sound or if the user 101 enters a response indicating that the user 101 cannot hear the sound, the mobile device 103 may cause the over-ear headphones 104 to play the sound with an increased amplitude at a predetermined interval (e.g., 5 dB steps). By repeating the increase and decrease of the amplitude of the sound, the mobile device 103 may obtain a threshold audible amplitude where the user 101 can hear for each frequency.

Based on the threshold amplitude for each frequency, the hearing aid 102 may further perform calibration for each frequency to provide relatively equalized amplitudes across frequencies by compensation of sound pressure for each frequency. The threshold amplitudes for frequencies as another profile of the user 101 together with the sound profile of the sound source may also be stored in the mobile device 103. In some embodiments, the profile of the user 101 together with the sound profile of the sound source may also be transmitted to the remote server 108 via the communications link 107 and the remote server 108 may record the profile of the user 101. Once the calibration is performed, another hearing test may be performed to confirm the hearing improvement by the real-ear fitting 110.

Figure 2:
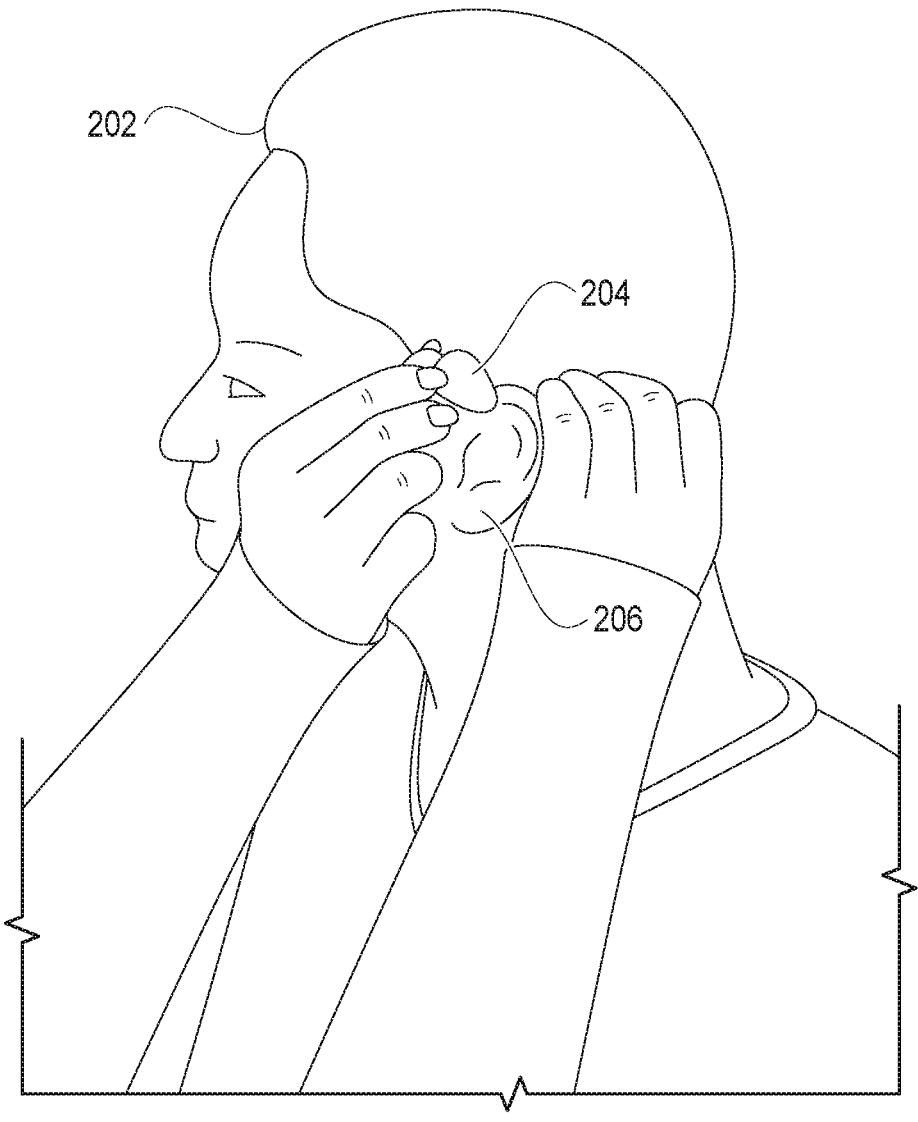
FIG. 2 is a pictorial view showing a user beginning a standard fitting in accordance with one embodiment.

The standard fitting preparation 105 will be described in detail referring to FIGS. 2-6. FIG. 2 is a pictorial view showing a user 202 beginning a standard fitting in accordance with one embodiment. The user 202 may be the user 101 of FIG. 1. The user 202 wears a hearing aid 204 on one ear 206 of the user 202. In some embodiments, the hearing aid 204 may be the hearing aid 102 of FIG. 1. In some embodiments, the user 202 may wear a pair of hearing aids on a pair of corresponding ears (e.g., a hearing aid with "L" on the left ear of the user 202, and a hearing aid with "R" on the right ear of the user 202). In some embodiments, the user 202 may wear one of the pair of hearing aids on one corresponding ear of the pair of ears. By wearing the hearing aid 204 on the corresponding ear 206, the standard fitting may be performed on the correct ear and the fitting result will be collected and recorded.

Figure 3:
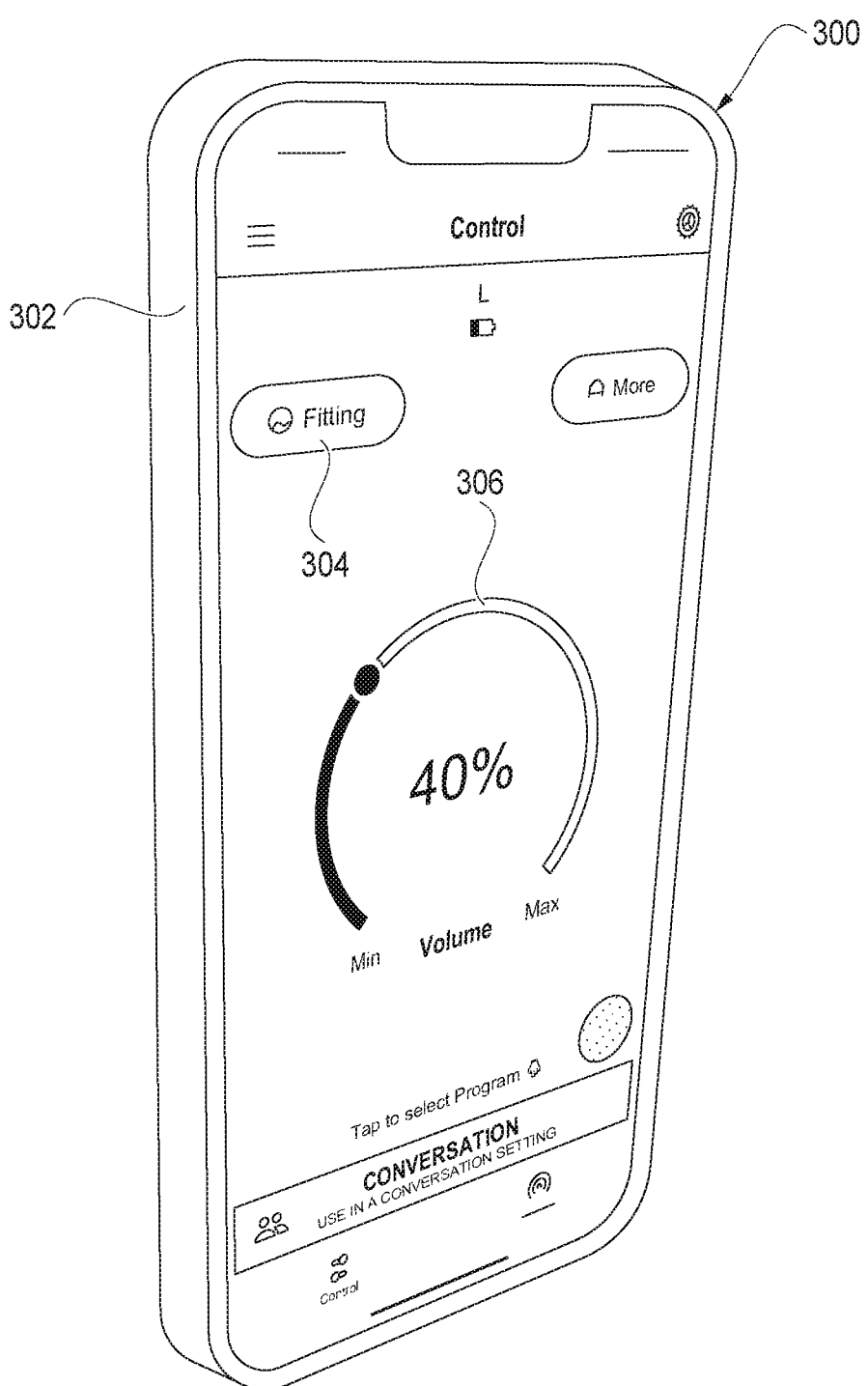
FIG. 3 is a screenshot showing a control screen in accordance with one embodiment.

FIG. 3 is a screenshot showing a control screen 302 of a computing device 300 in accordance with one embodiment. The user 202 may connect the hearing aid 204 with the computing device 300 (e.g., the mobile device 103) wirelessly (e.g., Bluetooth, NFC, Wi-Fi, etc.), or with one or more wires before or after wearing the hearing aid 204. In the example of FIG. 3, the control screen 302 includes a volume control interface 306 and an icon 304 indicating "fitting," prompting a user to start a hearing aid fitting process. When the icon 304 is tapped by a user, the computing device 300 may enter into a fitting process.

Figure 4:
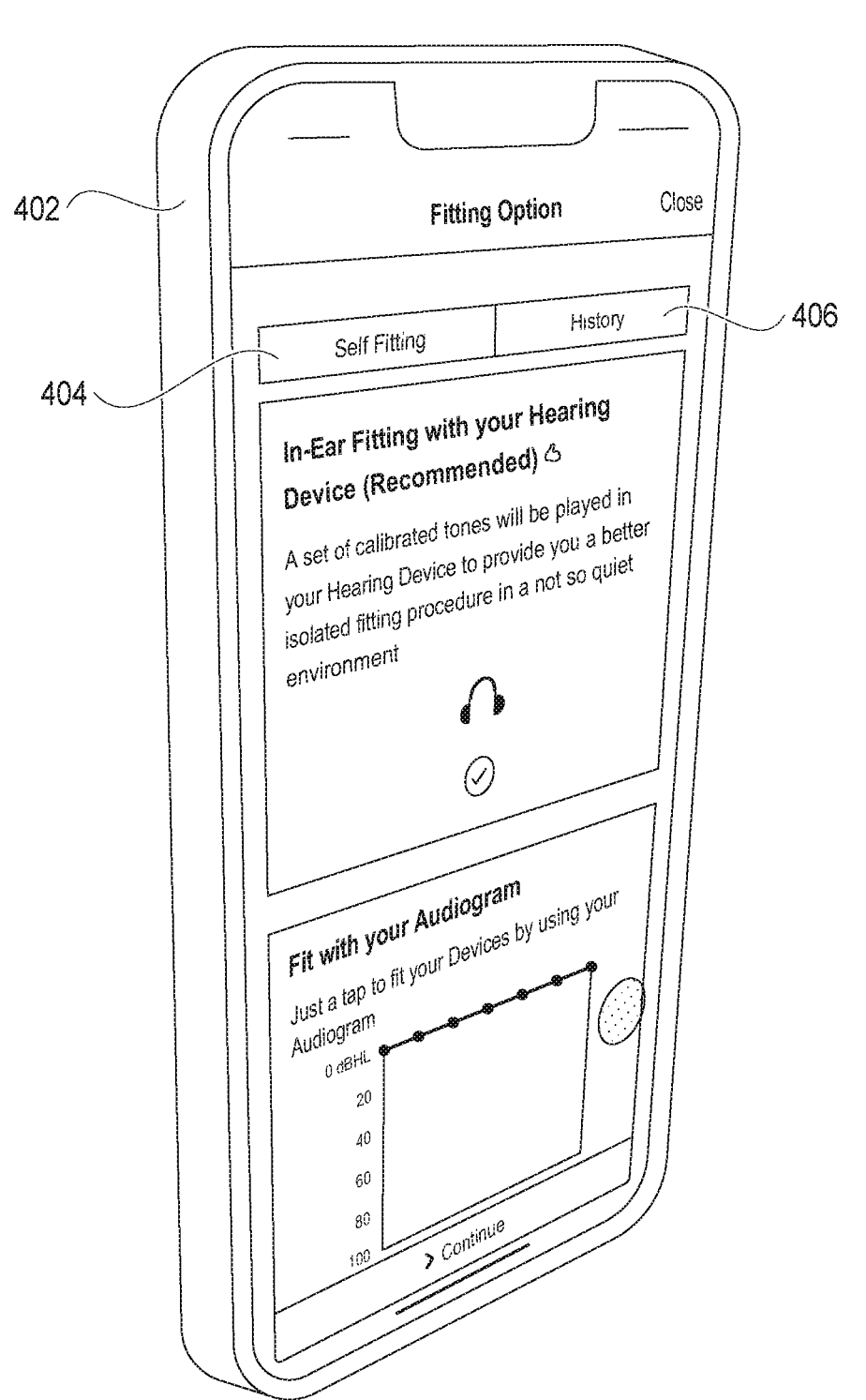
FIG. 4 is a screenshot showing an in-ear fitting screen for a standard fitting in accordance with one embodiment.

FIG. 4 is a screenshot showing an in-ear fitting screen 402 of the computing device 300 for a standard fitting in accordance with one embodiment. In some embodiments, the in-ear fitting screen 402 may be an initial screen that may describe an explanation of the in-ear fitting process to a user. In the example of FIG. 4, the in-ear fitting screen 402 includes an icon 404 indicating "Self-fitting" and an icon 406 indicating "History," prompting a user to select a fitting option between self-fitting and history-based fitting. If the icon 406 "History" is tapped by a user, the computing device 300 may read one or more past records of calibration history and/or sound environment history from any of the computing device 300 itself, the records previously provided by the hearing aid 204 or another hearing aid previously used, or the remote server 108.

Figures 5A, 5B:
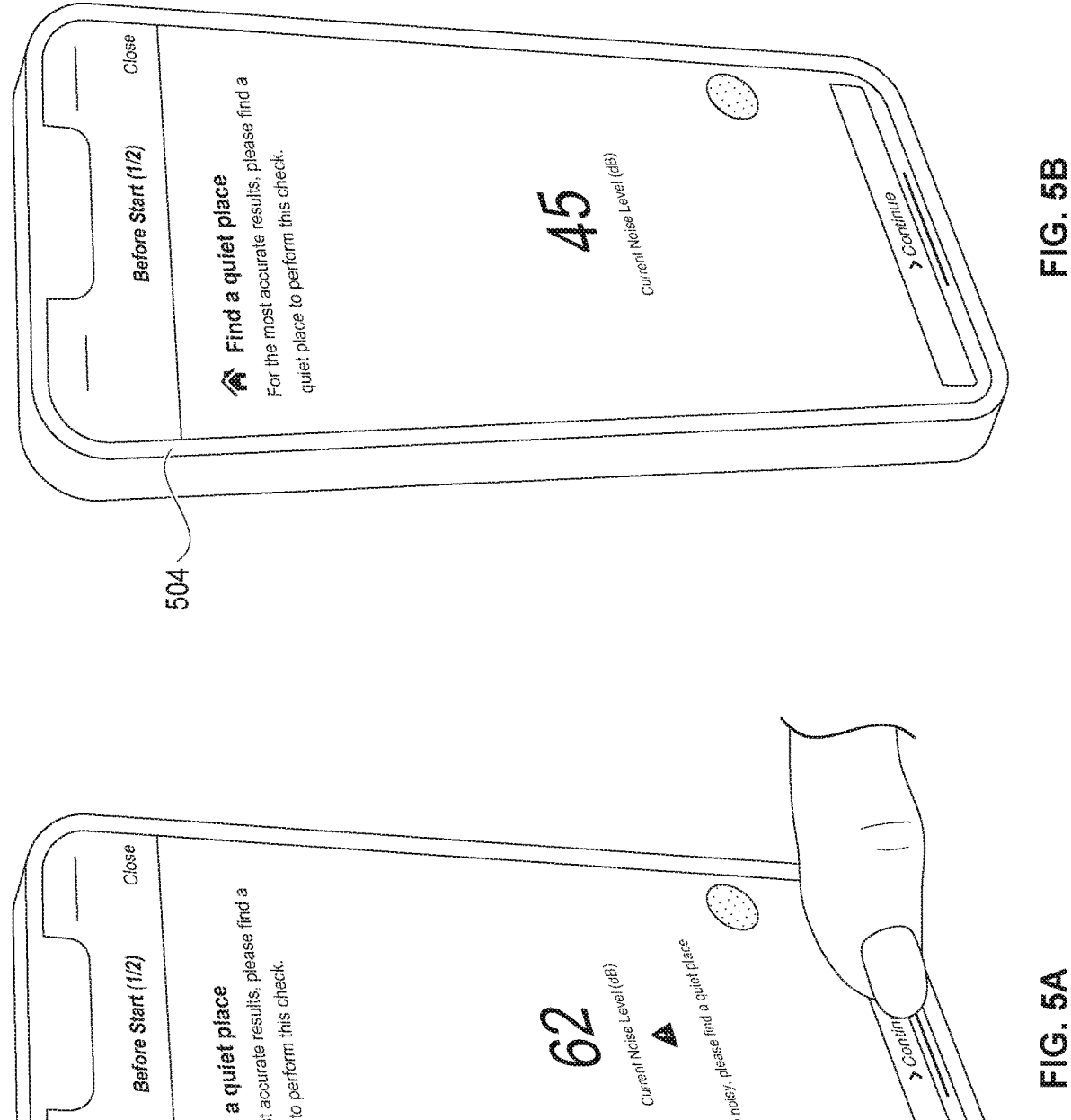
FIGS. 5A and 5B are screenshots showing ambient noise presentation screens in accordance with one embodiment.

FIGS. 5A and 5B are screenshots showing ambient noise presentation screens 502 and 504 in accordance with one embodiment. The ambient noise presentation screens 502 and 504 may prompt the user 202 to be in a quiet place with a noise level under a predetermined threshold sound pressure level. In the examples of FIGS. 5A and 5B, the predetermined threshold sound pressure level may be set to 50 dB; however, any predetermined sound pressure level suitable for a combination of hearing aid hardware specification and sound environment may be set for the room setting. In FIG. 5A, the screen 502 indicates that the ambient noise level is at 62 dB (above the predetermined threshold sound pressure level) and indicates an alert that prompts the user 202 to find a quiet place. In FIG. 5B, the screen 504 indicates that the ambient noise level is at 45 dB (below the predetermined threshold sound pressure level) without the alert.

Figure 6:
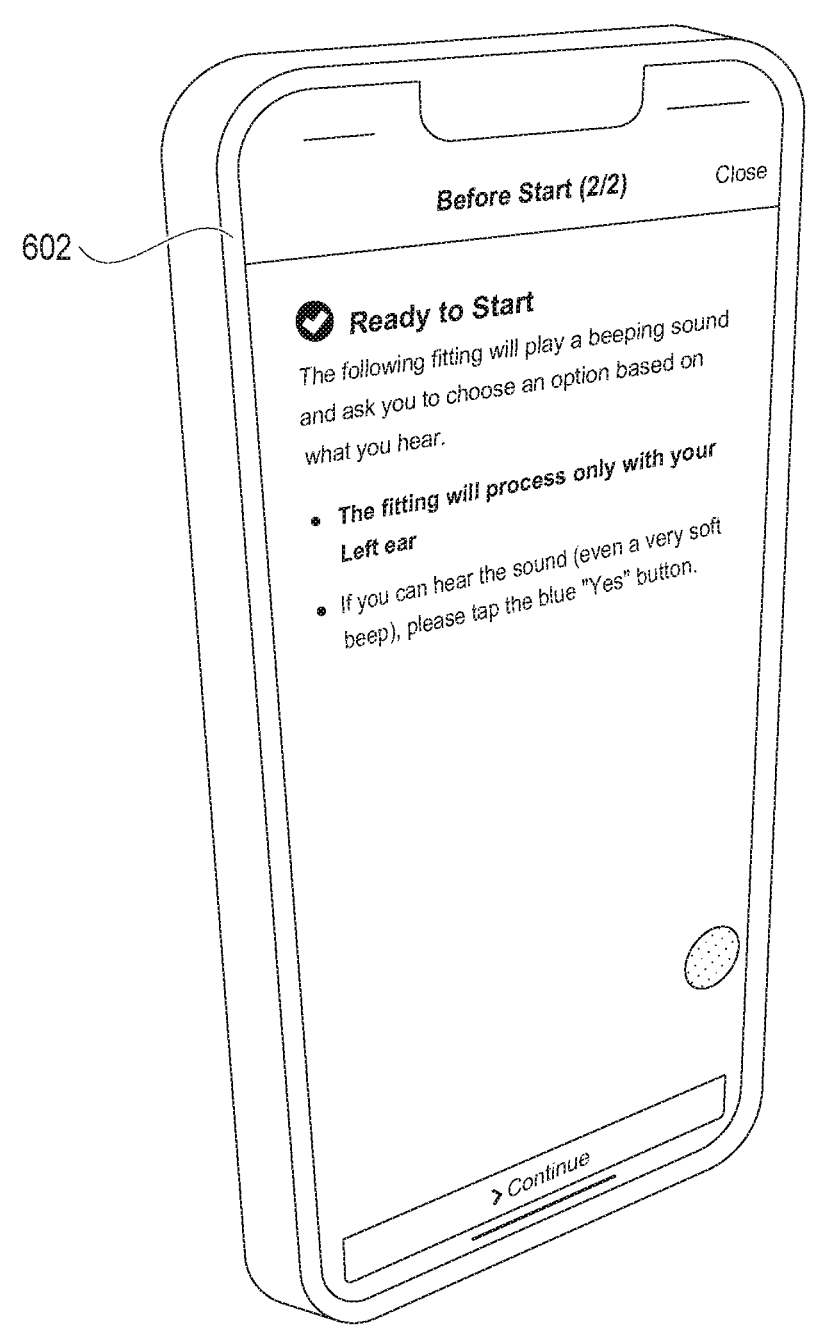
FIG. 6 is a screenshot showing a launch test screen in accordance with one embodiment.

FIG. 6 is a screenshot showing a launch test screen 602 in accordance with one embodiment. In the end of the standard fitting preparation 105, the launch test screen 602 may indicate that a system including the computing device 300 and the hearing aid 204 may be ready to start the standard fitting. In some examples, the launch test screen 602 may further provide instructions on how the standard fitting operates. The instructions indicate that the fitting will process one ear (e.g., a left ear) and a prompt may be provided to a user to select an option based on what the user hears or whether the user hears or does not hear a sound from the hearing aid 204.

The standard fitting 106 will be described in detail referring to FIGS. 7A-9.

Figures 7A, 7B, 7C:
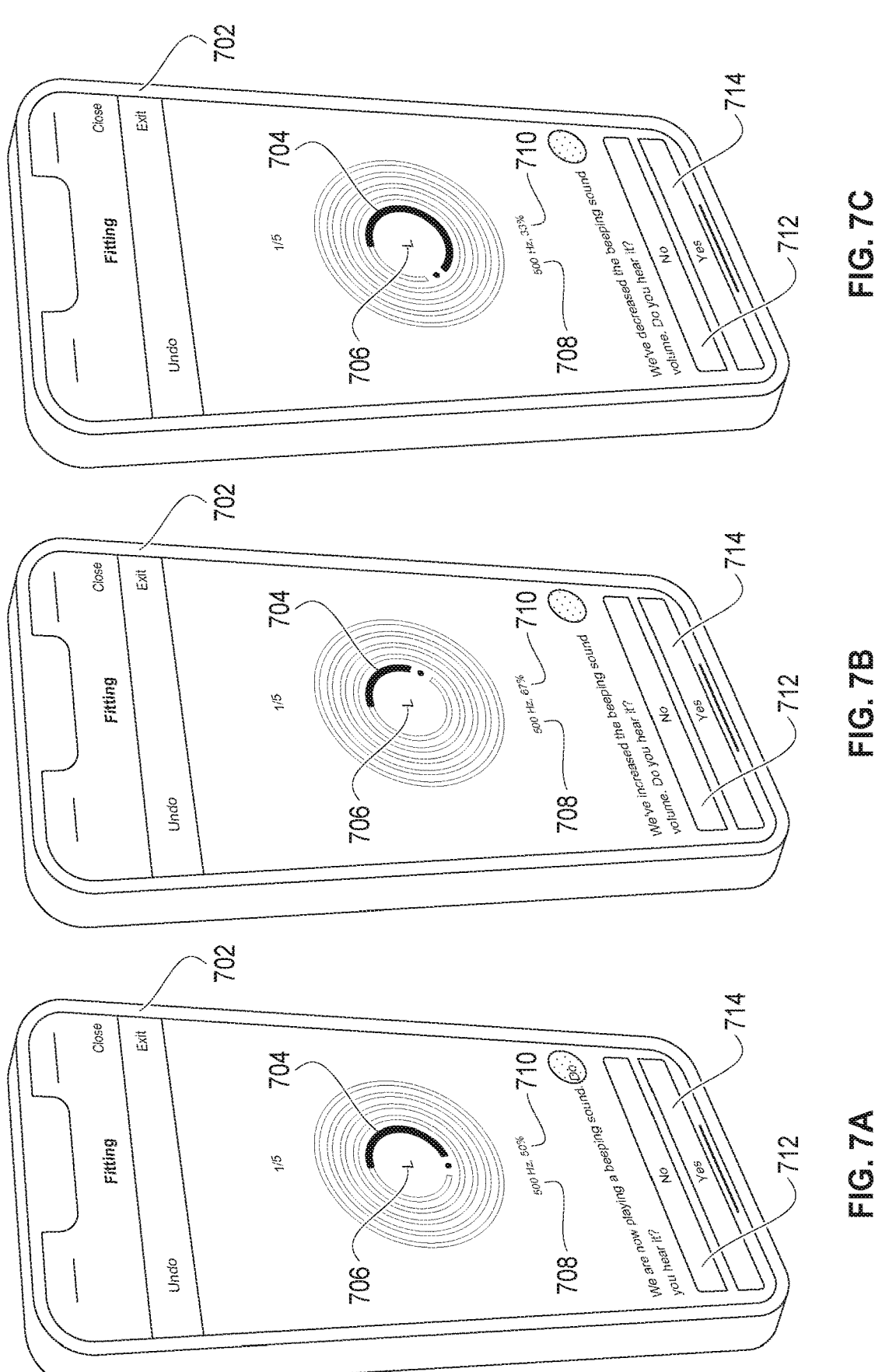
FIGS. 7A-7C are screenshots showing pure-tone hearing screens in accordance with one embodiment.

FIGS. 7A-7C are screenshots showing pure-tone hearing screens 702 in accordance with one embodiment.

Once a user starts an initial hearing test on the computing device 300, such as the mobile device 103, the computing device 300 may perform the initial hearing test by causing the hearing aid 204 to play a sound at a frequency based on the standard protocol equivalent to pure-tone threshold audiometry taught in the ASLH guidelines for multiple frequencies. In some embodiments, the hearing aid 204 may store sound signals at the above predetermined frequencies used for the initial hearing test, and the computing device 300 may transmit a command instructing the hearing aid 204 to play a sound at one of these frequencies in the protocol, and the hearing aid 204 may play the sound. In some embodiments, the computing device 300 may provide a sound signal at each of these frequencies in the protocol, and the hearing aid 204 may play the sound.

The hearing aid 204 plays the sound for each frequency at a reference amplitude for a predetermined time (e.g., 1-2 seconds). In some embodiments, the computing device 204 may display a current frequency 708 and a current amplitude 710 of the sound being played on the screen 702. In FIG. 7A, the current frequency 708 is 500 Hz and the current amplitude 710 is 50% of a full amplitude. The current amplitude 710 may be displayed in a percentage in the screen 702; however, the current amplitude 710 may be displayed in dB. The computing device 300 may allow the user 202 to indicate whether the user 202 can hear the sound. In some embodiments, the computing device 300 may display a time bar 704 that indicates an elapsed time of playing the sound and a currently tested ear L/R 706. In some examples, the computing device 300 may display response buttons, such as a No button 712 and a Yes button 714 on the screen 702. If the user 202 enters a response indicating that the user cannot hear the sound by tapping the No button 712, the computing device 300 may cause the hearing aid 204 to play the sound with an increased amplitude at a predetermined interval (e.g., 5 dB steps). In this example of FIG. 7B, the current amplitude 710 is increased from 50% to 67%. If the user 202 enters a response indicating that the user 202 can hear the sound by tapping the Yes button 714, the computing device 300 may cause the hearing aid 204 to play the sound with a reduced amplitude at a predetermined interval (e.g., −5 dB steps). In this example of FIG. 7C, the current amplitude 710 is decreased from 50% to 33%. By repeating the increase and decrease of the amplitude of the sound, the computing device 300 may obtain a threshold audible amplitude that is the lowest decibel hearing level that the user 202 can hear for each frequency.

Based on the threshold amplitude for each frequency, the hearing aid 204 may perform calibration for each frequency to provide relatively equalized amplitudes across frequencies by compensation of sound pressure for each frequency. The threshold amplitudes for frequencies as a profile of the user 202 may also be stored in the computing device 300.

Figure 9:
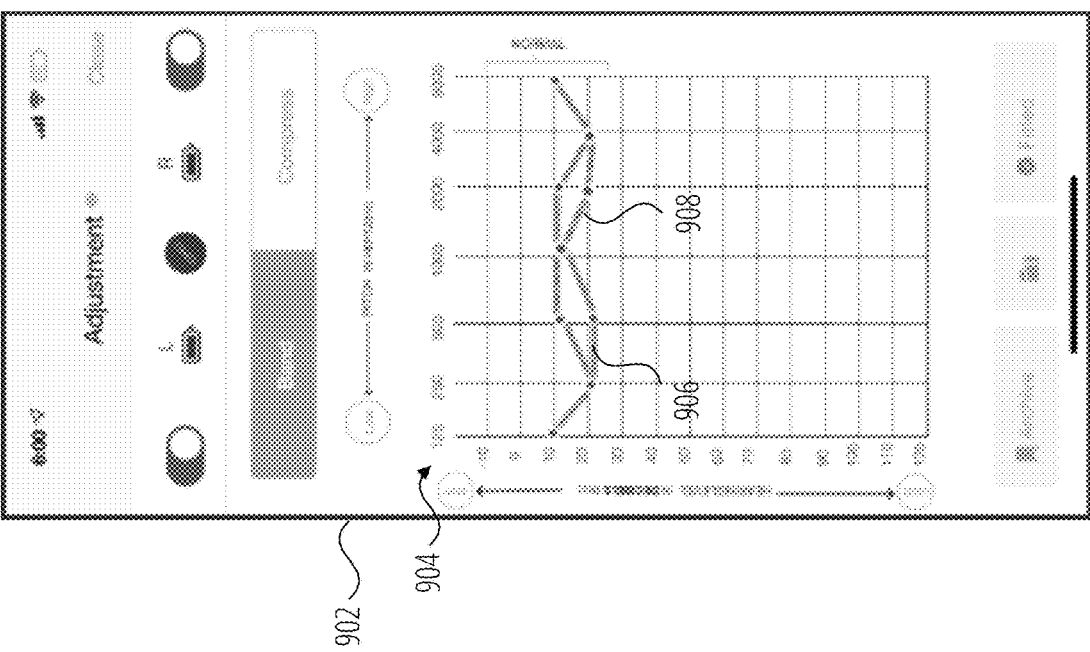
FIGS. 8 and 9 are screenshots showing audiograms before and after standard fitting in accordance with one embodiment.
Figure 8:
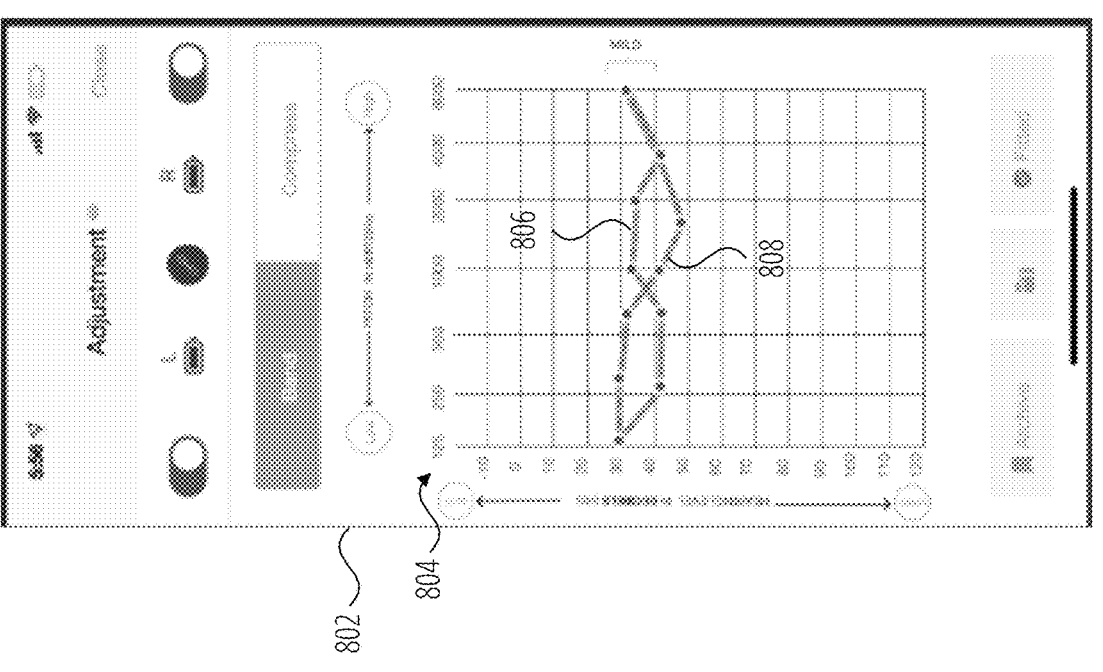

FIGS. 8 and 9 are screenshots 802 and 902, respectively, showing audiograms 804 and 904, respectively, before and after standard fitting, respectively. In each audiogram of the audiograms 804 and 904, a horizonal axis represents pitch levels shown in frequency ranges from 125 Hz to 8,000 Hz, and a vertical axis represents hearing levels in sound pressure level ranges from 120 dB at the bottom to −10 dB at the top. If the hearing is better, a lower dB sound can be heard, and thus a result for the better hearing is plotted higher in each of the audiograms. In FIGS. 8 and 9, each of the audiograms 804 and 904 includes plots obtained for each of the left and right ears at frequencies connected by lines for each ear.

The screenshot 802 includes the audiogram 804 indicating a hearing test result without hearing aid calibration. The audiogram 804 may include a line 806 connecting plots for a left ear and a line 808 connecting plots for a right ear. At 250 Hz and 500 Hz, the right ear hears 30 dB whereas the left ear hears 40 dB only. At 1,000 Hz and near 2,000 Hz, the left ear hears just below 30 dB whereas the right ear hears 40 dB and 50 dB, respectively. The screenshot 802 may further indicate a hearing level tendency indicating "mild" hearing loss.

The screenshot 902 includes the audiogram 904 indicating a hearing test result with hearing aid calibration. The audiogram 904 may include a line 906 connecting plots for the left ear and a line 908 connecting plots for the right ear. At 500 Hz, the right ear hears 10 dB whereas the left ear hears 20 dB only. At 2,000 Hz, the left ear hears just below 10 dB whereas the right ear hears 20 dB. The screenshot 902 may further indicate a hearing level tendency indicating "normal" hearing range. The user 202 may be able to see improvement in hearing after the calibration using hearing aid 204 by looking at the audiograms 804 and 904.

The real-ear fitting preparation 109 will be described in detail referring to FIG. 10.

Figure 10:
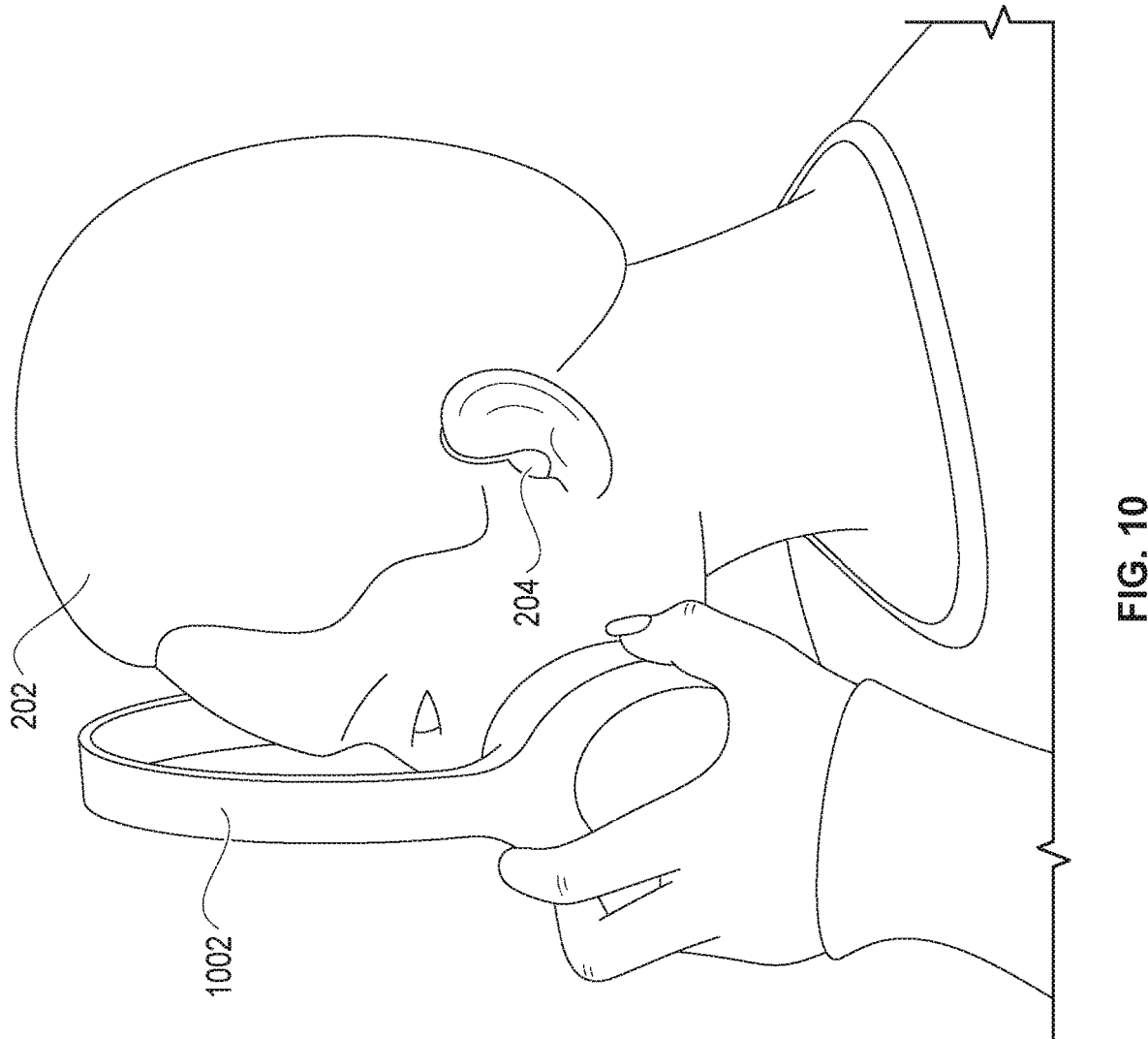
FIG. 10 is a pictorial view showing a user beginning a real-ear fitting in accordance with one embodiment.

FIG. 10 is a pictorial view showing the user 202 beginning a real-ear fitting in accordance with one embodiment. The user 202 may be exposed to a sound source outside the hearing aid 204. In some examples, the user 202 may wear over-ear headphones 1002, such as the over-ear headphones 104, as a sound source over the hearing aid 204 as shown in FIG. 10. In another example, the user 202 may be in a room with a sound source (e.g., a speaker).

The sound source, such as the over-ear headphones 1002, may provide sound, as if providing a sound to a real ear. The hearing aid 204 may receive the sound from the over-ear headphones 1002, and amplify the sound based on the calibration performed in the standard fitting. In some embodiments, the computing device 300, such as the mobile device 103 or the remote server 108, may have access to a sound profile, such as frequency response characteristics of the over-ear headphones 1002, or the sound source and/or the room, and further calibrate the hearing aid 204.

The real-ear fitting 110 will be described in detail referring to FIGS. 11A, 11B, and 12.

Figure 11A:
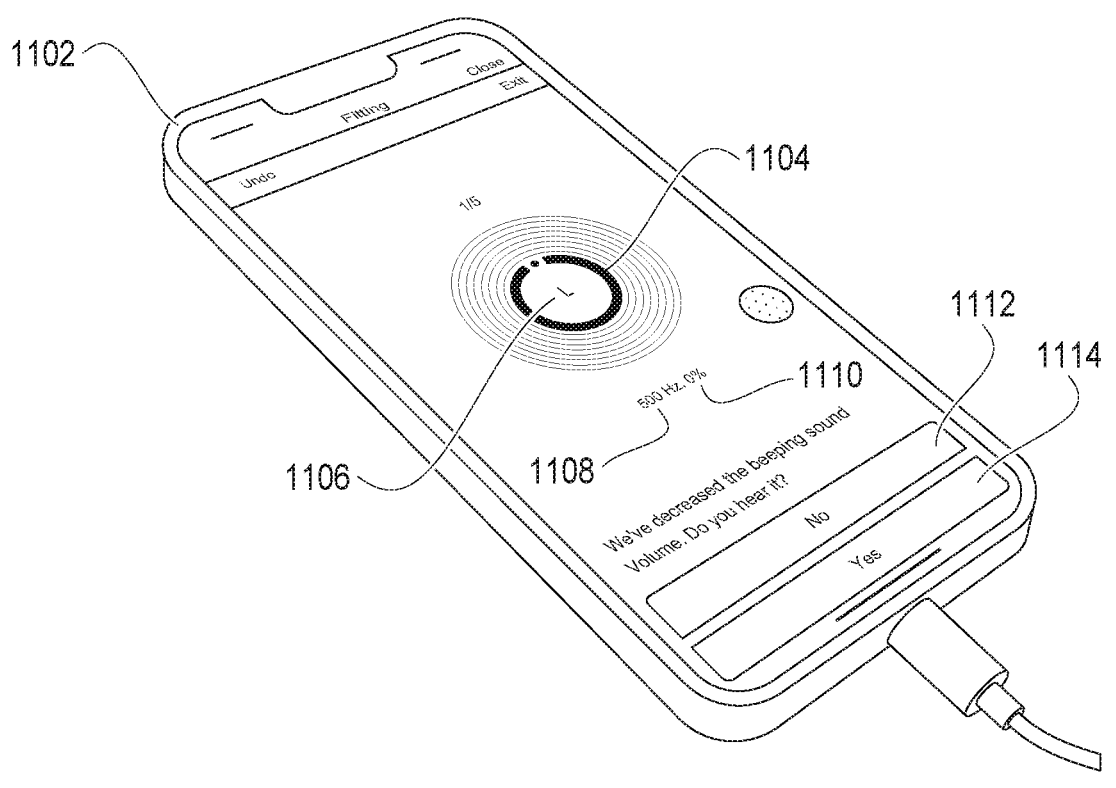
FIGS. 11A-11B are screenshots showing pure-tone hearing screens in accordance with one embodiment.
Figure 11B:
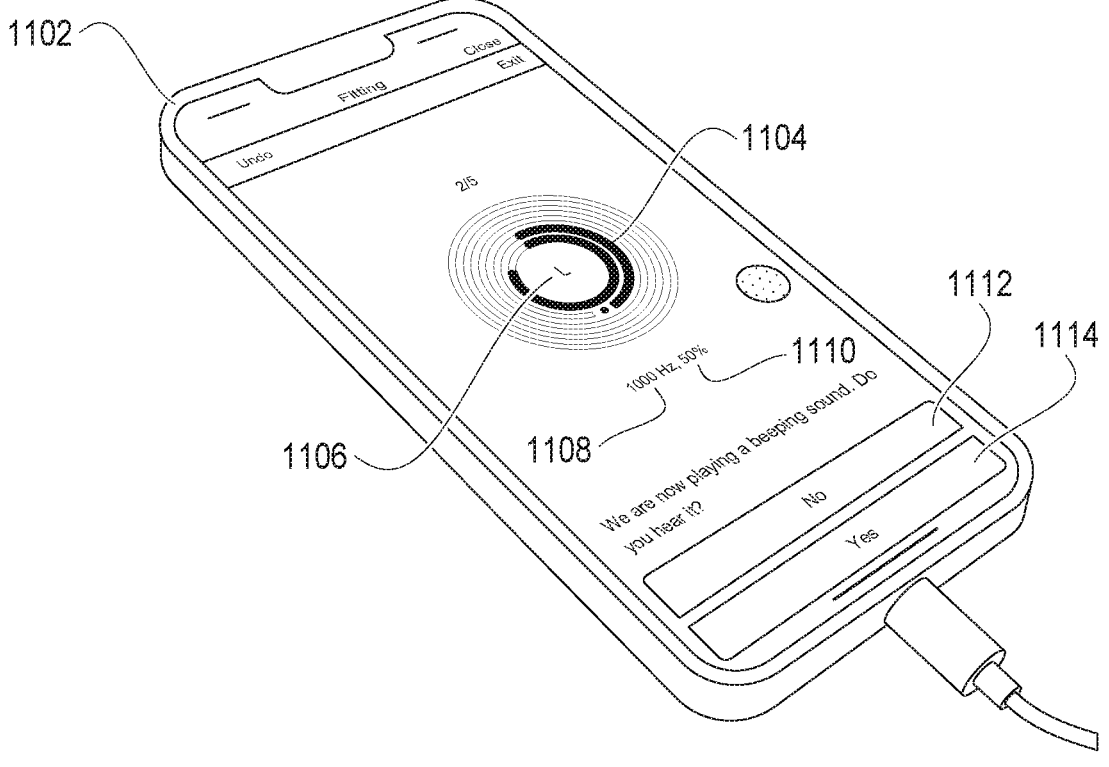

FIGS. 11A-11B are screenshots showing pure-tone hearing screens 1102 in accordance with one embodiment.

Once a user starts a real-ear hearing test on the computing device 300, such as the mobile device 103, the computing device 300 may perform the real-ear hearing test by causing the sound source, such as the over-ear headphones 1002, to play a sound at a frequency based on the standard protocol. In some embodiments, the over-ear headphones 1002 may store sound signals at the above predetermined frequencies used for the initial hearing test, and the computing device 300 may transmit a command instructing the over-ear headphones 1002 to play a sound at one of these frequencies in the protocol, and the over-ear headphones 1002 may play the sound. In some embodiments, the computing device 300 may provide a sound signal at each of these frequencies in the protocol, and the over-ear headphones 1002 may play the sound.

The over-ear headphones 1002 plays the sound for each frequency at a reference amplitude for a predetermined time (e.g., 1-2 seconds). In some embodiments, the computing device 300 may display a current frequency 1108 and a current amplitude 1110 of the sound being played on the screen 1102. In FIG. 11A, the current frequency 1108 is 500 Hz and the current amplitude 1110 is 0% of a full amplitude. The current amplitude 1110 may be displayed in a percentage on the screen 702; however, the current amplitude 1110 may be displayed in dB. The computing device 300 may allow the user 202 to indicate whether the user 202 can hear the sound. In some embodiments, the computing device 300 may display a time bar 1104 that indicates an elapsed time of playing the sound and a currently tested ear L/R 1106. In some examples, the computing device 300 may display response buttons, such as a No button 1112 and a Yes button 1114 on the screen 1102. If the user 202 enters a response indicating that the user 202 cannot hear the sound by tapping the No button 1112, the computing device 300 may cause the hearing aid 204 to play the sound with an increased amplitude at a predetermined interval (e.g., 5 dB steps). In this example of FIG. 11B, the current amplitude 1110 is increased from 0% to 17%. If the user 202 enters a response indicating that the user 202 can hear the sound by tapping the Yes button 1114, the computing device 300 may cause the hearing aid 204 to play the sound with a reduced amplitude at a predetermined interval (e.g., −5 dB steps). By repeating the increase and decrease of the amplitude of the sound, the computing device 300 may obtain a threshold audible amplitude that is the lowest decibel hearing level that the user 202 can hear for each frequency in the real-ear fitting.

Based on the threshold amplitude for each frequency, the hearing aid 204 may perform calibration for each frequency to provide relatively equalized amplitudes across frequencies by compensation of sound pressure for each frequency. The threshold amplitudes for frequencies as a profile of the user 202 may also be stored in the computing device 300.

Once the calibration is performed, another hearing test may be performed to confirm the hearing improvement by the real-ear fitting 110.

Figure 12:
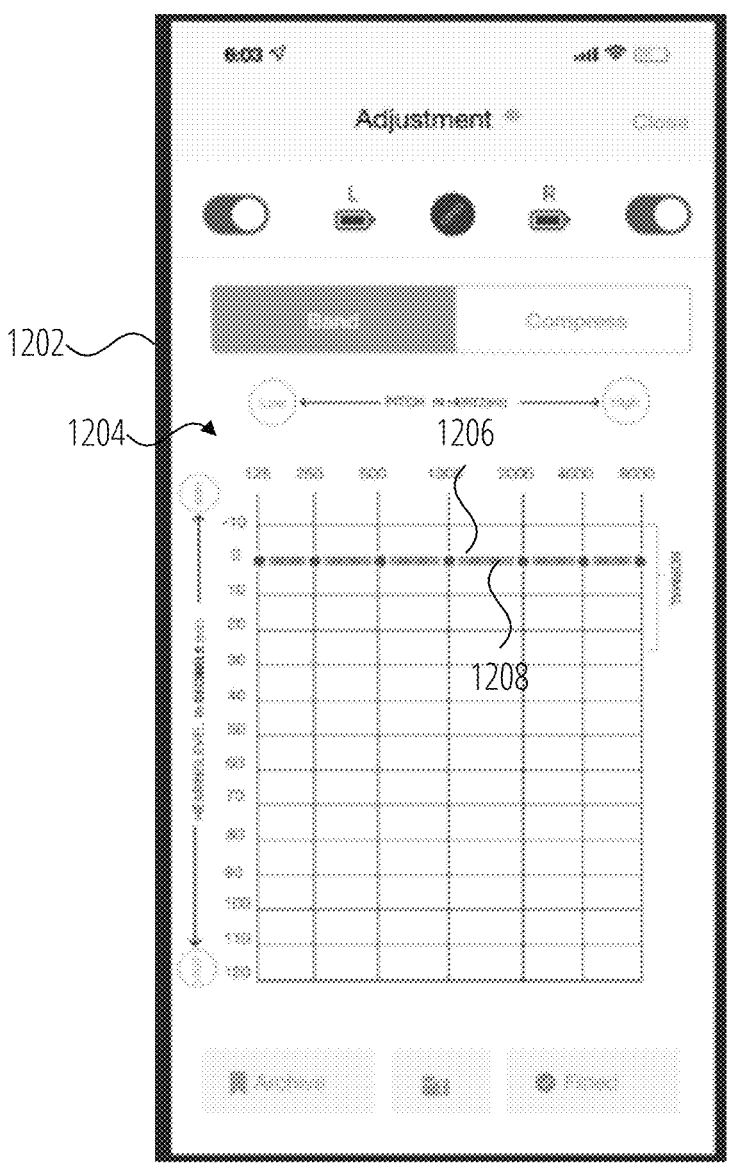
FIG. 12 is a screenshot showing an audiogram after real-ear fitting in accordance with one embodiment.

FIG. 12 is a screenshot 1202 showing an audiogram 1204 after real-ear fitting. In the audiogram 1204, a horizonal axis represents pitch levels shown in frequency ranges from 125 Hz to 8,000 Hz, and a vertical axis represents hearing levels in sound pressure level ranges from 120 dB at the bottom to −10 dB at the top. If the hearing is better, a lower dB sound can be heard and thus a result for the better hearing is plotted higher in each of the audiograms. In FIG. 12, the audiogram 1204 includes plots obtained for each of the left and right ears at frequencies connected by lines for each ear. The audiogram 1204 indicates a hearing test result without hearing aid calibration after real-ear fitting. The audiogram 1204 may include a line 1206 connecting plots for a left ear and a line 1208 connecting plots for a right ear. All the plots show that the right and left ears hear 0 dB at all frequencies tested. The lines 1206 and 1208 are straight lines at 0 dB, indicating that there is no gap between hearing at the same frequency between the right and left ears. The user 202 may be able to see improvement in hearing after the calibration using hearing aid 204 by looking at the audiograms 904 and 1204. The screenshot 1202 may further indicate a hearing level tendency indicating a "normal" hearing range.

Figure 13:
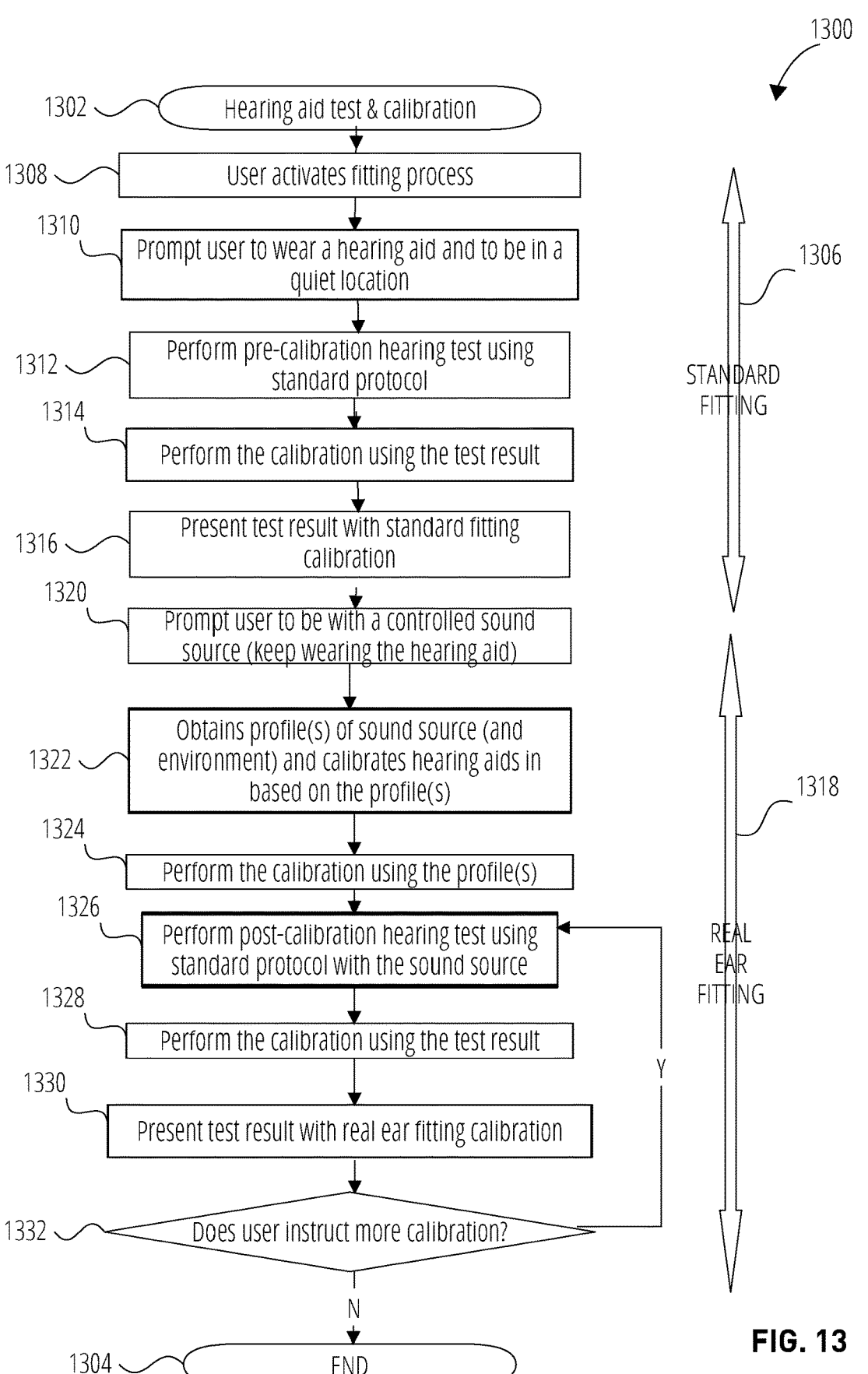
FIG. 13 shows an example process 1300 for performing a hearing test and calibration of a hearing aid, according to one embodiment.

FIG. 13 shows an example process 1300 for performing a hearing test and calibration of a hearing aid, according to one embodiment. The process 1300 includes standard fitting 1306 including steps 1308-1316, and real-ear fitting 1318 including steps 1320-1332. Once the process 1300 starts at step 1302, a user, such as the user 202, may activate a fitting process in a hearing aid app on a computing device, such as the mobile device 103 or the computing device 300, at step 1308. Throughout the process 1300, the app may prompt the user to perform actions by causing instructions to the user to be displayed on a screen and/or announcing instructions to the user through a speaker or headphones, etc. Alternatively, the instructions may be distributed to the user as a printed manual or an online manual.

In step 1310, the computing device may prompt the user to wear one hearing aid or a pair of hearing aids, and further prompt the user to be at a quiet location. In some embodiments, the user may be prompted to enter a sound-proofed kiosk or other similar structure containing a calibrated sound system with one or more sound sources. In some embodiments, the hearing aid may be the hearing aid 102 or the hearing aid 204. If the app on the computer device determines that the hearing aid is detecting a consistent noise level in the location, the app may proceed to step 1312 to perform a pre-calibration hearing test using a standard protocol. After the test is performed, the app may present test results by showing the pre-calibration result, such as the audiogram 804. Alternatively, instead of performing the pre-calibration hearing test, the user may instruct the app to use the "history" without running the pre-calibration hearing test, and then the app may read the past test result and use the past test result as the test result.

Once the test is conducted or the past test result is obtained, the app may proceed to step 1314 to perform calibration of the hearing aid using the test result. In some embodiments, the calibration may be performed frequency by frequency immediately after obtaining the test result for each frequency. In some embodiments, the calibration may be performed for multiple frequencies after obtaining the test results for the multiple frequencies. After the calibration is performed, the app may proceed to step 1316 to present test results with standard fitting and calibration, by showing the post-calibration result, such as the audiogram 904. In some embodiments, the audiogram 904 may be presented together with the audiogram 804 for comparison.

Next, the app may proceed to real-ear fitting 1318. In the beginning of the real-ear fitting 1318, the app may allow the user to be with a controlled sound source while still wearing the hearing aid. In some embodiments, the user may be prompted to wear the over-ear headphones 104 or the over-ear headphones 1002. In some other embodiments, the user may be prompted to enter a sound-proofed kiosk or other similar structure containing a calibrated sound system with one or more sound sources. Once the user confirms that the user is with a controlled sound source, the app may proceed to step 1322, and the app may obtain profile(s) of sound source (and environment) internally in the app, from a remote server, such as the remote server 108, or on the internet. The app may calibrate the hearing aid based on the obtained profile in step 1324. This sound profile-based calibration may be optional.

The app may proceed to step 1326 to perform a post-calibration hearing test using a standard protocol while the sound is provided by the sound source. Once the test is conducted, the app may proceed to step 1328 to further perform calibration of the hearing aid using the result of the test using the sound source. In some embodiments, the calibration may be performed frequency by frequency immediately after obtaining the test result for each frequency. In some embodiments, the calibration may be performed for multiple frequencies after obtaining the test results for the multiple frequencies. After the calibration is performed, the app may proceed to step 1330 to present test results with real-ear fitting and calibration, by showing the post-calibration result, such as the audiogram 1204. In some embodiments, the audiogram 1204 may be presented together with the audiogram 904 for comparison. If the user is not content with the result, the user may instruct more calibration in step 1332. If the user instructs more calibration ("Y"), the app may proceed back to the step 1326 to conduct recalibration. If the user is content ("N"), the real-ear fitting 1318 is complete and the fitting ends at step 1304.

The recalibration may be done as many times to calibrate the hearing aid or alternatively may be done for a specific number of iterations after which the user may be informed that the hearing aids cannot be calibrated to completely compensate for their specific hearing loss profile. In this case the user may be prompted to return the hearing aids or alternatively may choose to retain them and use them with the calibration being of a sufficient degree to allow the user to hear the frequencies they desire to hear at a level that while not "normal" is "good enough."

In some embodiments, the sound environment may be recorded while the user is using the hearing aid. The recorded historical sound environment data may be used by executing a neural network algorithm to learn the user's sound environment over time and build a model that may be used for performing post-calibration adjustment by fine-tuning based on the user's sound environment that may be different from the test environment.

FIG. 14 shows an example process 1400 for performing a hearing test and calibration using the standard protocol, according to one embodiment. In some embodiments, the process 1400 may be used for performing the steps 1312 and 1314 of the standard fitting 1306 or the steps 1326 and 1328 in the real-ear fitting 1318.

Once the process 1400 starts at step 1402, the app on a computing device, such as the mobile device 103 or the computing device 300, may set a default frequency for test and calibration at step 1404 and set a default amplitude for test and calibration at step 1406. In some embodiments, the default amplitude may be set relatively low following the ASLH guidelines for protecting ears. Then the app may proceed to step 1408 to cause a screen, such as the screen 702 or the screen 1102, to display the frequency as the frequency 708 or the frequency 1108, and the amplitude as the amplitude 710 or the amplitude 1110 in step 1408. The app may start the hearing test, such as the tests in the step 1312 and/or the step 1326, by causing the computing device running the app to provide a command to play a sound at the set frequency and the amplitude at step 1410. In some embodiments, the computing device may provide the command to the hearing aid in the step 1312. In some embodiments, the computing device may provide the command to the sound source, such as the headphones or a speaker in a room of the controlled sound environment in the step 1326. Responsive to the command, the hearing aid or the sound source may play a sound at the set frequency and the amplitude at step 1412. While the sound is played, the computing device may also prompt a user to respond to indicate whether the user can hear the sound. In some embodiments, the Yes button and the No button may be displayed on the screen to prompt the user to respond by interacting with one of these buttons on the screen, such as tapping, touching, pressing, etc. In some embodiments, the user may be prompted to type certain letters to indicate the response. In some embodiments, the user may be prompted to respond by using input devices, such as a mouse, clickers, etc. The computing device may receive a response by the user in step 1414 and the app may proceed to step 1416. If the response is "cannot hear" or no response indicative of "can hear" in a predetermined period (e.g., while the sound is being played) ("N"), the app may send a command to increase the amplitude to the hearing aid or the sound source at step 1418, and the app may proceed back to the step 1408 to display the frequency and the increased amplitude on the screen and continue. In some embodiments, increasing the amplitude may cause calibration in the hearing aid of step 1314 or step 1328. In some embodiments, increasing the amplitude by the sound source may not lead to calibration in the hearing aid, and the hearing aid calibration may be performed separately after all the hearing test results are obtained in step 1328.

If the response is "can hear" ("Y"), the test and adjustment of amplitude by calibration for the frequency is complete and the app may proceed to step 1420. In some embodiments, after receiving the response indicative of "can hear" ("Y"), the app may decrease (not shown) and increase the amplitude to confirm a boundary of "can hear" and "cannot hear." Once the boundary between "can hear" and "cannot hear" is determined, the app may check whether tests and calibration are for all the frequencies is complete in step 1420. If there is any predetermined frequency for the test not used for the test ("N"), then the user may change the frequency to the untested one, and proceed back to the step 1404 and continue. If all the frequencies are tested and calibrated ("Y") in the step 1420, the app may proceed to step 1422 to cause a screen, such as the screen 702 or the screen 1102, to display that the test and calibration is complete, and the hearing aid is ready to use.

This iteration process may be done as many times as is necessary to calibrate the hearing aids or alternatively may be done for a specific number of iterations after which the user may be informed that the hearing aids cannot be calibrated to completely compensate for their specific hearing loss profile. In this case the user may be prompted to return the hearing aids or alternatively may choose to retain them and use them with the calibration being of a sufficient degree to allow the user to hear the frequencies they desire to hear at a level that while not "normal" is "good enough."

Operations of processes described herein can be performed in any suitable order unless otherwise indicated herein or otherwise clearly contradicted by context. Processes described herein (or variations and/or combinations thereof) may be performed under the control of one or more computer systems configured with executable instructions and may be implemented as code (e.g., executable instructions, one or more computer programs, or one or more applications) executing collectively on one or more processors, by hardware, or combinations thereof. The code may be stored on a computer-readable storage medium—for example, in the form of a computer program comprising a plurality of instructions executable by one or more processors. The computer-readable storage medium may be non-transitory.

Figure 15:
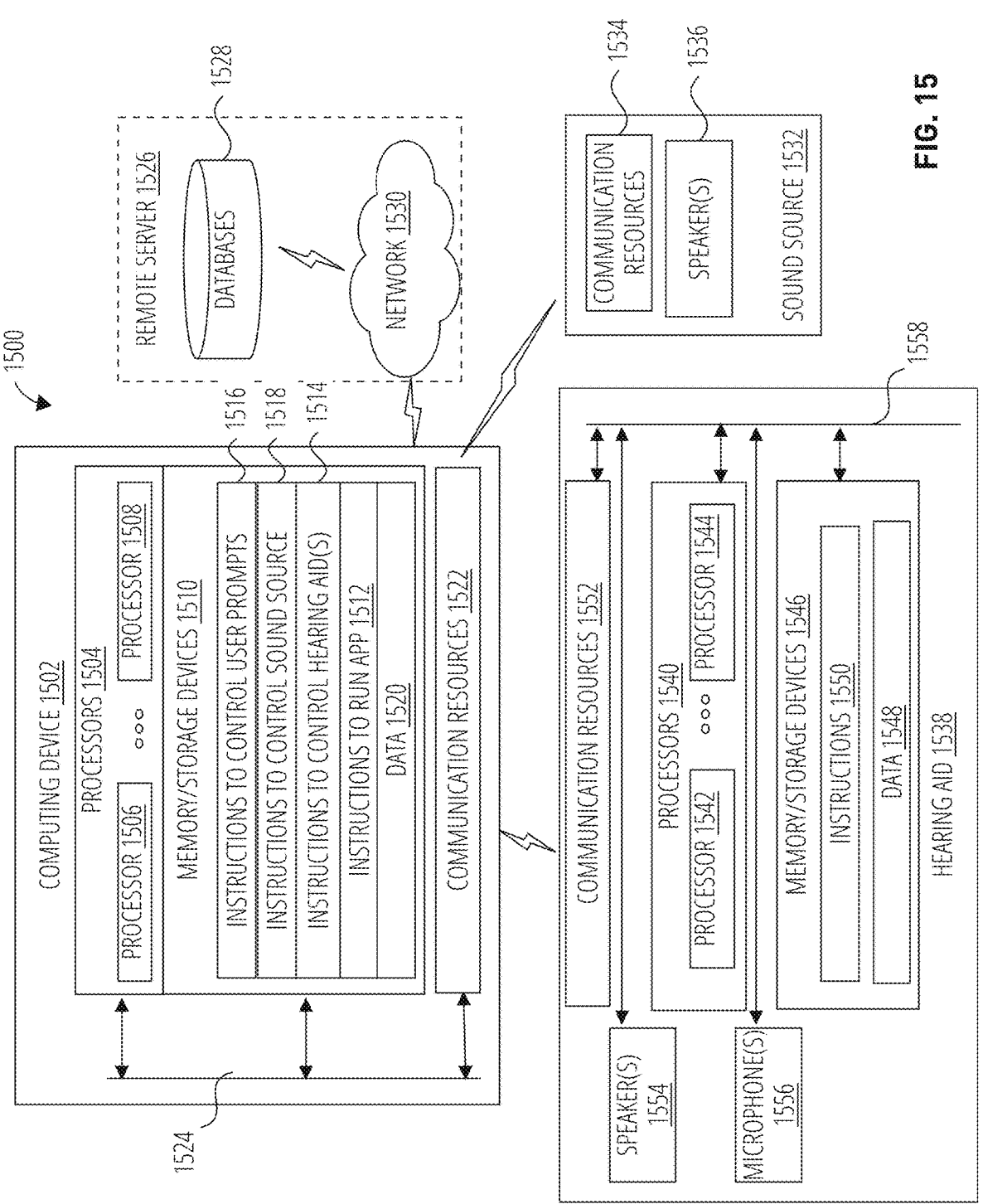
FIG. 15 is a block diagram of a hearing aid hearing test and calibration system in accordance with one embodiment.

FIG. 15 is a block diagram of a hearing aid hearing test and calibration system 1500 in accordance with one embodiment. The system 1500, according to some example embodiments, may be able to read instructions from a machine-readable or computer-readable medium (e.g., a non-transitory, machine-readable storage medium) and perform any one or more of the methods discussed herein, such as process 1300 in FIG. 13 and/or process 1400 in FIG. 14.

Specifically, FIG. 15 shows a diagrammatic representation of the system 1500 including a computing device 1502, a sound source 1532, and a hearing aid 1538. The sound source 1532 and the hearing aid 1538 may be coupled to the computing device 1502, wirelessly (e.g., Bluetooth, NFC, Wi-Fi, etc.) and/or with one or more wires (e.g., a Universal Serial Bus (USB)). The sound source 1532 may be coupled to the computing device 1502 by analog audio cables. The system 1500 may further include a remote server 1526, which may be connected to the computing device 1502 via network 1530, such as the internet or an intranet.

The computing device 1502 may include one or more processors 1504 (or processor cores), one or more memory/storage devices 1510, and one or more communication resources 1522, each of which may be communicatively coupled via a bus 1524.

The one or more processors 1504 may include, for example, a processor 1506 and a processor 1508. The one or more processors 1504 may include, for example, a central processing unit (CPU), a reduced instruction set computing (RISC) processor, a complex instruction set computing (CISC) processor, a graphics processing unit (GPU), a digital signal processor (DSP) such as a baseband processor, an application specific integrated circuit (ASIC), another processor, or any suitable combination thereof.

The memory/storage devices 1510 may include main memory, disk storage, or any suitable combination thereof. The memory/storage devices 1510 may include, but are not limited to, any type of volatile or non-volatile memory such as dynamic random-access memory (DRAM), static random-access memory (SRAM), erasable programmable read-only memory (EPROM), electrically erasable programmable read-only memory (EEPROM), Flash memory, solid-state storage, etc. The memory/storage devices 1510 may store software, a program, an application, an applet, an app, or other executable code including instructions for causing at least one of the processors 1504 to perform any one or more of the methods discussed herein. The instructions may include, for example, instructions to run app 1512 performing the standard fitting 1306 and the real-ear fitting 1318, instructions to control user prompts 1516 (e.g., a screen of the mobile device 103, an external display device connected to the computer device 1502, a prompter connected to the computer device 1502, a speaker of the mobile device 103, a speaker connected to the computer device 1502, etc.), instructions to control hearing aid(s) 1514, and instructions to control sound source 1518. The instructions may reside, completely or partially, within the memory/storage devices 1510, or any suitable combination thereof. The instructions may further reside, completely or partially, within at least one of the processors 1504 (e.g., within the processor's cache memory). Furthermore, any portion of the instructions may be transferred to computing device 1502 from any combination of hearing aid 1538 or databases 1528 in the remote server 1526. Accordingly, the memory of processors 1504, memory/storage devices 1510 in the computing device 1502, memory/storage devices 1546 of the hearing aid 1538, and/or databases 1528 in the remote server 1526 may be examples of computer-readable and machine-readable media. The memory/storage devices 1510 may also store data 1520 that may include hearing test results and calibration history of the user, sound profile of sound environment of the user, sound profiles including frequency response characteristics of the hearing aid, the sound source, such as over-ear headphones, or a combination of a room and a speaker in the room, etc. that may be used for calibration.

The one or more communication resources 1522 may include interconnection or network interface components or other suitable devices to communicate with one or more hearing aid 1538, the sound source 1532, or one or more databases 1528 via a network 1530. For example, the communication resources 1522 may include wired communication components (e.g., for coupling via a USB), cellular communication components, NFC components, Bluetooth components (e.g., Bluetooth Low Energy), Wi-Fi components, and other communication components.

The sound source 1532 may include speaker(s) 1536 that may play sound in the real-ear fitting 1318. In some embodiments, the sound source 1532 may be a speaker in a room as a controlled sound environment. In some embodiments, the sound source 1532 may be over-ear headphones, such as the over-ear headphones 1002.

In some embodiments, the sound source 1532 may receive audio information to play sound wirelessly or via one or more wires. In some embodiments, the one or more communication resources 1534 may include interconnection or network interface components or other suitable devices to communicate with the computing device 1502. For example, the communication resources 1534 may include wired communication components (e.g., for coupling via a USB), cellular communication components, NFC components, Bluetooth components (e.g., Bluetooth Low Energy), Wi-Fi components, and other communication components.

In some embodiments, the over-ear headphones may include one or more microphones that may receive ambient sound and noise, and one or more processors (not shown), such as DSPs, may play sound to ears while cancelling the ambient noise. The over-ear headphones may be integrated with the hearing aid 1538 to perform noise cancelling headphones as well as hearing aids to amplify ambient sound without playing sound from another source.

The hearing aid 1538 may include one or more processors 1540 (or processor cores), one or more memory/storage devices 1546, one or more communication resources 1552, one or more microphones 1556, and one or more speakers 1554, each of which may be communicatively coupled via a bus 1558.

The one or more processors 1540 may include, for example, a processor 1542 and a processor 1544. The one or more processors 1540 may include, for example, a CPU, a RISC processor, a CISC processor, a GPU, a DSP such as a baseband processor, an ASIC, another processor, or any suitable combination thereof.

The memory/storage devices 1546 may include main memory, disk storage, or any suitable combination thereof. The memory/storage devices 1546 may include, but are not limited to, any type of volatile or non-volatile memory such as DRAM, SRAM, EPROM, EEPROM, Flash memory, solid-state storage, etc. The memory/storage devices 1546 may store software, a program, an application, an applet, an app, or other executable code including instructions 1550 for causing at least one of the processors 1540 to perform any one or more of the methods discussed herein. The instructions 1550 may include, for example, instructions to play a sound from the speaker(s) 1554 at a certain frequency after amplifying the sound at a certain amplitude by one or more processors 1540, such as DSPs, instructions to collect ambient sound from the microphone, and present the ambient sound from the speaker(s) 1554 after processing and amplifying the sound based on the calibration result by one or more processors 1540, such as DSPs. The instructions may reside, completely or partially, within the memory/storage devices 1546, or any suitable combination thereof. The instructions may further reside, completely or partially, within at least one of the processors 1540 (e.g., within the processor's cache memory). Furthermore, any portion of the instructions may be transferred to the hearing aid 1538 from any combination of the computing device 1502 or databases 1528 in the remote server 1526. Accordingly, the memory of processors 1540, memory/storage devices 1546 in the hearing aid 1538, memory/storage devices 1510 of the computing device 1502, and/or databases 1528 in the remote server 1526 may be examples of computer-readable and machine-readable media. The memory/storage devices 1546 may also store data 1548 that may include hearing test audio data and current calibration setting, or multiple calibration settings for each user, or different users, etc.

The one or more communication resources 1552 may include interconnection or network interface components or other suitable devices to communicate with the computing device 1502 or one or more databases 1528 via a network 1530. For example, the communication resources 1552 may include wired communication components (e.g., for coupling via a USB), cellular communication components, NFC components, Bluetooth components (e.g., Bluetooth Low Energy), Wi-Fi components, and other communication components. The communication resources 1552 may receive commands, instructions, and/or audio data from the computing device 1502.

In some embodiments, the hearing aid 1538 may be over-ear headphones that may include one or more microphones that may receive ambient sound and noise, and one or more processors (not shown), such as DSPs, may play sound to ears while cancelling the ambient noise. The over-ear headphones may be integrated with the hearing aid 1538 to perform noise cancelling headphones as well as hearing aids to amplify ambient sound without playing sound from another source.

Skilled persons will appreciate that many changes may be made to the details of the above-described embodiments without departing from the underlying principles of the disclosure. The scope of the present invention should, therefore, be determined only by claims and equivalents thereof.

What is claimed is:

1. A system comprising:
a hearing aid configured to amplify sound and further configured to play the amplified sound;
a sound source;
a memory device configured to store one or more sound profiles of the sound source; and
a computing device configured to communicate with the hearing aid, the computing device configured to:
perform a first fitting process responsive to an activation, the first fitting process including:
setting a test frequency and a test amplitude;
causing the hearing aid to play a sound at the test frequency and the test amplitude;
prompting a user of the hearing aid to respond whether the user is able to hear; and
upon a positive or negative response from the user, causing the hearing aid to change the amplitude to calibrate;
perform a second fitting process after the first fitting process, the second fitting process including:
prompting the user to be with the sound source;
setting a second test frequency and a second test amplitude;
causing the sound source to play a sound at the second test frequency and the second test amplitude;
prompting the user to respond whether the user is able to hear; and
upon a positive or negative response from the user, causing the sound source to change the amplitude and further configured to calibrate the hearing aid,
wherein the computing device is configured to obtain at least one sound profile of the one or more sound profiles of the sound source, and further configured to calibrate the hearing aid based on the obtained at least one sound profile prior to the second fitting process.

2. The system of claim 1, wherein the memory device is incorporated in a remote server.

3. The system of claim 1, wherein the sound source is outside the hearing aid.

4. The system of claim 3, wherein the sound source is at least one of a speaker or an over-ear headphone.

5. The system of claim 1, wherein the computing device is a mobile device comprising a screen, and wherein the computing device is configured to prompt the user to perform an action by causing one or more instructions to the user to be displayed on the screen.

6. The system of claim 5, wherein the computing device is configured to display the frequency and the amplitude on the screen.

7. The system of claim 5, wherein the computing device is configured to prompt the user to perform an action by announcing instructions to the user.

8. The system of claim 1, wherein the computing device is further configured to store a user profile comprising one or more calibration results of the fitting process associated with the user.

9. The system of claim 8, further comprising a remote server, wherein the computing device is further configured to send the user profile to the remote server, and, wherein the remote server is configured to store the user profile and further configured to transmit the user profile upon a request from a hearing aid.

10. A non-transitory computer-readable storage medium comprising instructions that, when executed by one or more processors of a computing device, cause the computing device to perform a first fitting process comprising:

setting a test frequency and a test amplitude responsive to an activation;

causing a hearing aid to play a sound at the test frequency and the test amplitude;

prompting the user of the hearing aid to respond as to whether the user is able to hear the sound; and upon a positive or negative response from the user, causing the hearing aid to change the test amplitude to calibrate, cause the computing device to further perform a second fitting process comprising:

prompting the user to be with a sound source;

obtaining one or more profiles of the sound source;

calibrating the hearing aid based on the obtained one or more profiles of the sound source;

after calibrating the hearing aid, setting a second test frequency and a second test amplitude;

causing the sound source to play a sound at the second test frequency and the second test amplitude;

prompting the user to respond whether the user is able to hear; and upon a positive or negative response from the user, causing the sound source to change the amplitude and further configured to calibrate the hearing aid.

11. The non-transitory computer-readable storage medium of claim 10, wherein the fitting process is performed using a standard protocol.

12. The non-transitory computer-readable storage medium of claim 10, wherein the first or second fitting process further comprises:

if the response is positive, confirming a hearing threshold amplitude, including:

decreasing the test amplitude relative to the hearing threshold amplitude and prompting the user to respond as to whether the user is able to hear the sound, and repeating the decreasing step until the response is negative; and thereafter increasing the test amplitude relative to the hearing threshold amplitude and prompting the user to respond as to whether the user is able to hear the sound, and repeating the increasing step until the response is positive; and determining that calibration for the test frequency is complete if the hearing threshold amplitude is confirmed.

13. The non-transitory computer-readable storage medium of claim 12, wherein the fitting process further comprises storing a user profile comprising the hearing threshold for the test frequency.

14. The non-transitory computer-readable storage medium of claim 12, wherein the fitting process further comprises:

transmitting the user profile to a remote server; and storing the user profile at the remote server.

15. The non-transitory computer-readable storage medium of claim 12, wherein the first or second fitting process further comprises:

if there is another test frequency untested after the calibration for the test frequency is complete, performing the corresponding first or second fitting process at the untested test frequency until the calibration is performed for all the test frequencies.

16. The non-transitory computer-readable storage medium of claim 10, wherein the second fitting process further comprises:

presenting test results based on the second fitting process; and upon receiving an instruction from a user, repeat performing another second fitting process using test results of the prior second fitting process.

17. A method of performing a fitting process of a hearing aid, the method comprising:

responsive to an activation, during a first fitting process, setting a test frequency and a test amplitude;

causing the hearing aid to play a sound at the test frequency and the test amplitude;

prompting a user of the hearing aid to respond as to whether the user is able to hear the sound; and upon a positive or negative response from the user, causing the hearing aid to change the test amplitude to calibrate, following the first fitting process, performing a second fitting process comprising:

prompting the user to be with a sound source;

obtaining one or more profiles of the sound source;

calibrating the hearing aid based on the obtained one or more profiles of the sound source;

after calibrating the hearing aid, setting a second test frequency and a second test amplitude;

causing the sound source to play a sound at the second test frequency and the second test amplitude;

prompting the user to respond whether the user is able to hear; and upon a positive or negative response from the user, causing the sound source to change the amplitude and further configured to calibrate the hearing aid.

* * * * *